(12) United States Patent
Eguchi et al.

(10) Patent No.: US 9,773,937 B2
(45) Date of Patent: Sep. 26, 2017

(54) INFORMATION ACQUISITION APPARATUS

(71) Applicant: Seiko Epson Corporation, Tokyo (JP)

(72) Inventors: Tsukasa Eguchi, Matsumoto (JP); Hideto Ishiguro, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/004,212

(22) Filed: Jan. 22, 2016

(65) Prior Publication Data
US 2016/0218238 A1 Jul. 28, 2016

(30) Foreign Application Priority Data

Jan. 27, 2015 (JP) ................................ 2015-013022

(51) Int. Cl.
*H01L 31/12* (2006.01)
*F21V 8/00* (2006.01)
(Continued)

(52) U.S. Cl.
CPC .......... *H01L 31/125* (2013.01); *A61B 5/1455* (2013.01); *A61B 5/489* (2013.01); *A61B 5/681* (2013.01); *G02B 6/0031* (2013.01); *G02B 6/0078* (2013.01); *H01L 31/02327* (2013.01); *A61B 2562/0233* (2013.01); *A61B 2562/046* (2013.01)

(58) Field of Classification Search
CPC .......................... H01L 131/125; H01L 131/12
See application file for complete search history.

(56) References Cited

U.S. PATENT DOCUMENTS 5,893,364 A * 4/1999 Haar .................... A61B 5/0059
356/338
6,045,511 A 4/2000 Ott et al.
(Continued)

FOREIGN PATENT DOCUMENTS

EP 0728440 A2 8/1996
EP 0777119 A2 6/1997
(Continued)

OTHER PUBLICATIONS

Extended European Search Report for Application No. EP 16 15 2538 dated Jun. 1, 2016 (6 pages).

*Primary Examiner* — Moazzam Hossain
*Assistant Examiner* — Hajar Kolahdouzan
(74) *Attorney, Agent, or Firm* — Harness, Dickey & Pierce, P.L.C.

(57) ABSTRACT

An biological body information acquisition apparatus includes an imager including light emitting devices that are arranged in a plane and emit light toward a human body and light receiving devices that are arranged in a plane and receive light from the human body and a light guide plate that is layered on the imager on the side thereof facing the human body and has light transmissivity in the direction of a normal to the light receiving devices and the light emitting devices. The light guide has a first portion (holes) and a second portion (substrate) that are arranged in a plane and have refractive indices different from each other. The first portion (holes) is so disposed as to coincide with the light receiving devices in a plan view, and the second portion (substrate) is so disposed as to coincide with the light emitting devices in the plan view.

7 Claims, 12 Drawing Sheets

(51) Int. Cl.
*H01L 31/0232* (2014.01)
*A61B 5/1455* (2006.01)
*A61B 5/00* (2006.01)

(56) References Cited

U.S. PATENT DOCUMENTS

| | | |
|---|---|---|
| 6,418,339 B1 | 7/2002 | Essenpreis et al. |
| 2006/0013013 A1 | 1/2006 | Hirata et al. |
| 2008/0097172 A1* | 4/2008 | Sawada .................. G01N 21/49 |
| | | 600/310 |
| 2008/0159599 A1 | 7/2008 | Kajihara et al. |
| 2013/0237860 A1 | 9/2013 | Ince |

FOREIGN PATENT DOCUMENTS

| | | |
|---|---|---|
| JP | 2008-165742 A | 7/2008 |
| JP | 2012-217570 A | 11/2012 |

* cited by examiner

INFORMATION ACQUISITION APPARATUS

BACKGROUND

1. Technical Field

The present invention relates to an information acquisition apparatus.

2. Related Art

There is a proposed information acquisition apparatus that measures a specific component in the blood in a noninvasive, optical manner (blood sugar level and alcohol component, for example) (see JP-A-2012-217570, for example). The information acquisition apparatus (biological body information generation apparatus) described in JP-A-2012-217570 is configured as follows: A biological body is irradiated with light emitted from a light emitting device (organic EL device); part of the light scattered in the biological body is received as reflected light with a light receiving device; and image information on a blood vessel, information representing whether a specific component is contained in the blood, and other types of information are acquired.

When the light received with the light receiving device contains a large amount of light (noise light) other than light (signal light) originally intended to be incident on the light receiving device, the signal-to-noise ratio (S/N ratio) undesirably decreases, resulting in difficulty acquiring image information on a blood vessel, information representing whether a specific component is contained in the blood, and other types of information. It is therefore desired to provide information acquisition apparatus in which a light receiving device receives light having a large S/N ratio.

SUMMARY

An advantage of some aspects of the invention is to solve at least a part of the problems described above, and the invention can be implemented as the following forms or application examples:

Application Example 1

An information acquisition apparatus according to this application example includes an imager including a light emitting device that emits light toward an object and a light receiving device that receives light from the object and a light guide plate that is so provided as to be layered on the imager on the side thereof facing the object. The light guide plate has light transmissivity in a direction in which the light guide plate is layered on the imager and has a first portion and a second portion having refractive indices different from each other. The first portion is so disposed as to coincide with the light receiving device when viewed in the direction, and the second portion is so disposed as to coincide with the light emitting device when viewed in the direction.

According to the configuration described above, the light guide plate is layered on the imager, which has the light emitting device and the receiving device, on the side thereof facing the object. The light guide plate has light transmissivity in the direction in which the light guide plate is layered on the imager and has the first portion and the second portion having refractive indices different from each other. The first portion is so disposed as to coincide with the light receiving device when viewed in the direction described above, and the second portion is so disposed as to coincide with the light emitting device when viewed in the direction described above. Therefore, light emitted from the light emitting device passes through the second portion of the light guide plate and travels toward the object, and light scattered and reflected in the object passes through the first portion of the light guide plate and travels toward the light receiving device. Since the refractive indices of the first and second portions differ from each other, at least one of the emitted light and the reflected light behaves as follows: That is, at least part of light traveling obliquely with respect to the direction described above is reflected off the interface between the first portion and the second portion. When the emitted light that obliquely travels is reflected off the interface between the first portion and the second portion, the amount of emitted light that enters the object increases, and the amount of emitted light that is reflected off the interface with the object to form noise light decreases. On the other hand, when reflected light that obliquely exits out of the object and is not directed to the light receiving device is reflected off the interface between the first portion and the second portion, the amount of reflected light guided to the light receiving device (signal light) increases. As a result, the S/N ratio of the light received with the light receiving device can be improved.

Application Example 2

In the information acquisition apparatus according to the application example described above, it is preferable that the refractive index of the first portion is smaller than the refractive index of the second portion.

According to the configuration described above, since the refractive index of the first portion is smaller than the refractive index of the second portion, at least part of the light obliquely traveling from the second portion toward the first portion is reflected off the interface between the second portion and the first portion. Further, the light traveling from the second portion and obliquely incident on the first portion is refracted at an angle of refraction greater than the angle of incidence. Therefore, when the light so emitted from the light emitting device as to diffuse in all directions and traveling obliquely with respect to the direction described above is incident from the second portion of the light guide plate on the first portion thereof, at least part of the emitted light is reflected off the interface between the first portion and the second portion. Further, the emitted light obliquely incident from the second portion of the light guide plate on the first portion thereof is refracted toward the side where the angle of the refracted light with respect to the direction described above decreases. Therefore, the amount of emitted light that enters the object increases, and the amount of emitted light that is reflected off the interface with the object to form noise light decreases. As a result, the S/N ratio of the light received with the light receiving device is improved.

Application Example 3

In the information acquisition apparatus according to the application example described above, it is preferable that the light guide plate is provided with a hole along the direction, in which the light receiving device and the light emitting device are arranged, and that the hole forms the first portion and a remaining portion of the light guide plate other than the hole forms the second portion.

According to the configuration described above, the hole provided in the light guide plate forms the first portion, and the remaining portion of the light guide plate forms the second portion. Since air is present in the first portion, the refractive index of the first portion can be smaller than the refractive index of the second portion.

Application Example 4

In the information acquisition apparatus according to the application example described above, it is preferable that the refractive index of the first portion is greater than the refractive index of the second portion.

According to the configuration described above, since the refractive index of the first portion is greater than the refractive index of the second portion, at least part of the light obliquely traveling from the first portion toward the second portion is reflected. Therefore, when the reflected light from the object, which is signal light, travels obliquely with respect to the direction described above and is incident from the first portion of the light guide plate on the second portion thereof, at least part of the reflected light that obliquely travels is reflected off the interface between the first portion and the second portion and directed toward the light receiving device. Therefore, the reflected light that is signal light but is not directed toward the light receiving device if no light guide plate is present is guided by the light guide plate to the light receiving device, whereby the amount of light received with the light receiving device can be increased. As a result, the S/N ratio of the light received with the light receiving device is improved.

Application Example 5

In the information acquisition apparatus according to the application example described above, it is preferable that the light guide plate is provided with a hole along the direction, in which the light receiving device and the light emitting device are arranged, and that the hole forms the second portion and a remaining portion of the light guide plate other than the hole forms the first portion.

According to the configuration described above, the hole provided in the light guide plate forms the second portion, and the remaining portion of the light guide plate forms the first portion. Since air is present in the second portion, the refractive index of the first portion can be greater than the refractive index of the second portion.

Application Example 6

In the information acquisition apparatus according to the application example described above, it is preferable that a reflection film is formed at an interface between the first portion and the second portion.

According to the configuration described above, since the reflection film is formed at the interface between the first portion and the second portion, light traveling obliquely from the second portion toward the first portion and light traveling obliquely from the first portion toward the second portion are both totally reflected off the reflection film. Therefore, the amount of emitted light reflected off the interface to form noise light can be reduced, and the amount of signal light received with the light receiving device can be increased. As a result, the S/N ratio of the light received with the light receiving device is improved.

Application Example 7

In the information acquisition apparatus according to the application example described above, it is preferable that the reflection film is a metal film.

According to the configuration described above, the reflection film, which is a metal film, can reflect light incident thereon in a satisfactory manner.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments that embody the invention will be described below with reference to the drawings. The drawings used in the description are shown in an enlarged, reduced, or exaggerated form as appropriate that allows recognition of a portion to be described. Further, components other than those necessary for description are omitted in some cases.

In the following embodiments, for example, a description "on a substrate" means a case where an object is disposed in contact with the substrate, a case where an object is disposed with another object interposed between the object and the substrate, or a case where an object is so disposed that part of the object is in contact with the substrate and another object is interposed between the remainder of the object and the substrate.

In the description of the following embodiments, a biological body information acquisition apparatus that acquires information on blood in a biological body will be described as an example of an information acquisition apparatus.

First Embodiment

Information Acquisition Apparatus

Figure 1:
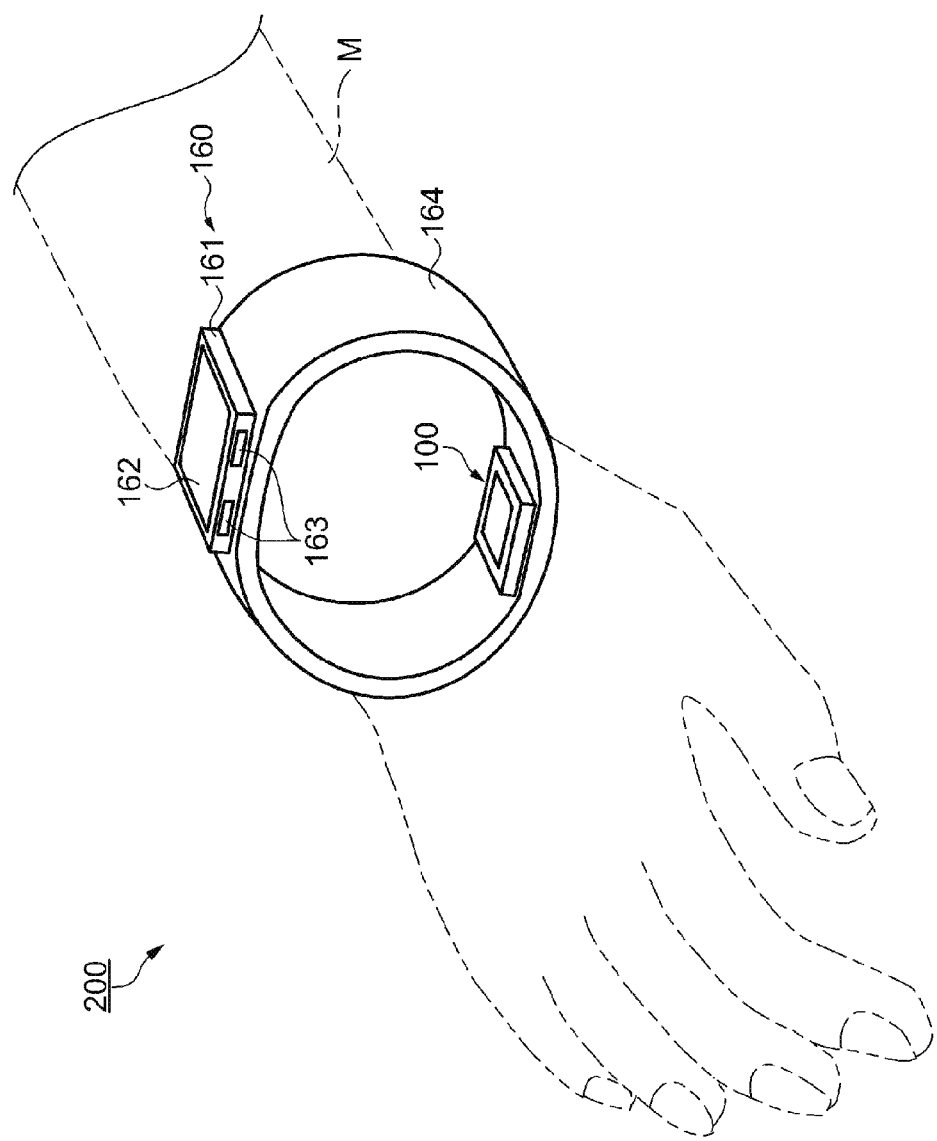
FIG. 1 is a perspective view showing the configuration of a biological body information acquisition apparatus as an example of an information acquisition apparatus according to a first embodiment.
Figure 2:
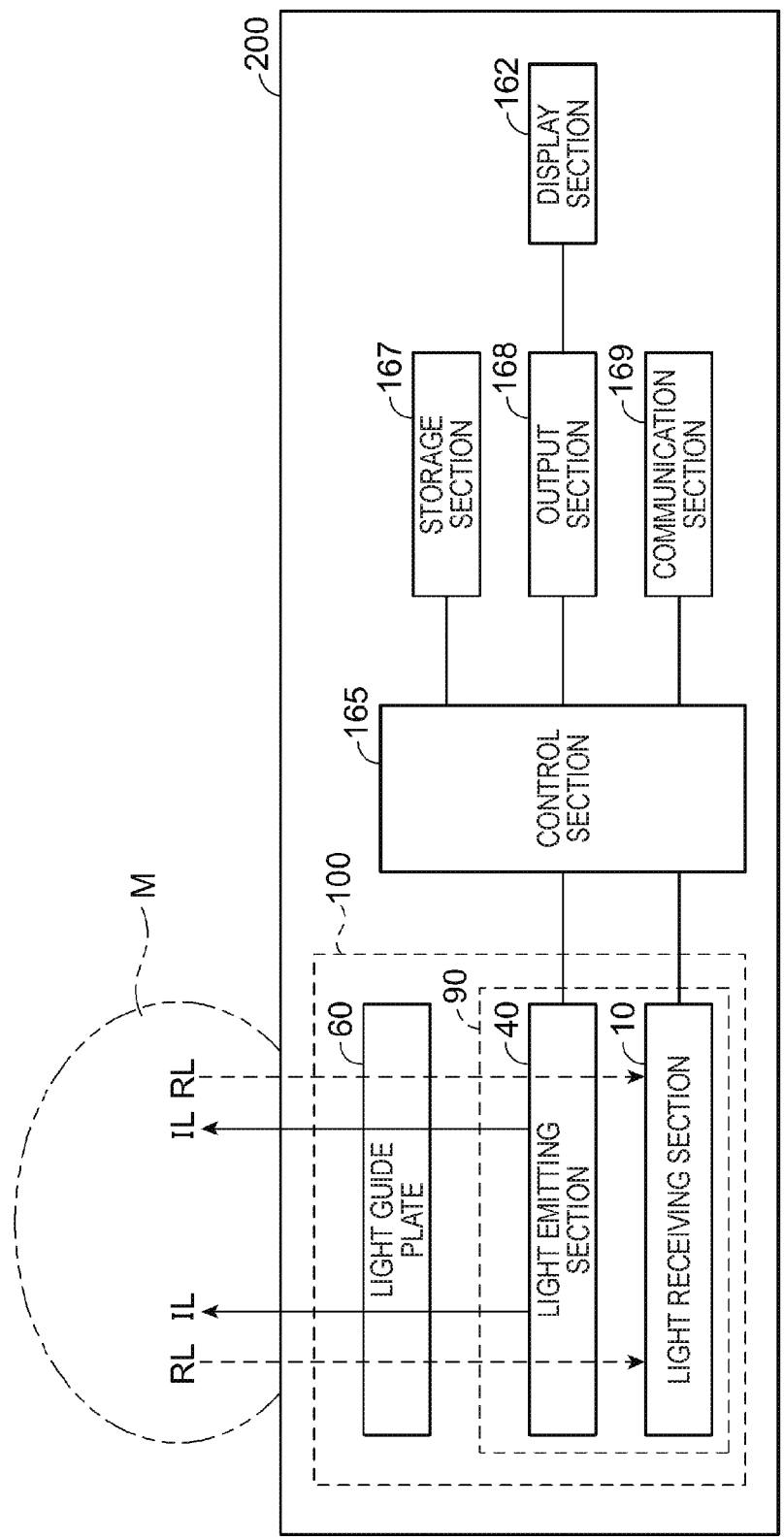
FIG. 2 is a block diagram showing the electrical configuration of the biological body information acquisition apparatus according to the first embodiment.

A biological body information acquisition apparatus as an example of an information acquisition apparatus according to a first embodiment will be described with reference to FIGS. 1 and 2. FIG. 1 is a perspective view showing the configuration of the biological body information acquisition apparatus as an example of the information acquisition apparatus according to the first embodiment. FIG. 2 is a block diagram showing the electrical configuration of the biological body information acquisition apparatus according to the first embodiment.

A biological body information acquisition apparatus 200 according to the present embodiment is a portable information terminal apparatus worn around a wrist of a biological body (human body) M as a target. The biological body information acquisition apparatus 200 can, on the basis of image information on a blood vessel inside the wrist, identify the position of the blood vessel in the biological body and identify the blood sugar level by detection of the content of a specific component, for example, glucose, in the blood in the blood vessel in a noninvasive, optical manner.

The biological body information acquisition apparatus 200 includes an annular belt 164, which can be worn around a wrist, a main body section 160, which is attached to the outer surface of the belt 164, and a sensor section 100, which is attached to the inner surface of the belt 164 in a position facing the main body section 160.

The main body section 160 has a main body case 161 and a display section 162, which is incorporated in the main body case 161. In the main body case 161 are incorporated operation buttons 163, a circuit system (see FIG. 2), such as a control section 165, which will be described later, a battery as a power supply, and other components as well as the display section 162.

The sensor section 100 is electrically connected to the main body section 160 via wiring (not shown in FIG. 1) incorporated in the belt 164. The sensor section 100 includes an imager 90 and a light guide plate 60 (see FIG. 2). The imager 90 includes a light emitting section 40 and a light receiving section 10 (see FIG. 4).

The thus configured biological body information acquisition apparatus 200 is so worn around a wrist when used that the sensor section 100 comes into contact with the wrist on the palm side, which is opposite the back of the hand. The thus worn information acquisition apparatus biological body 200 prevents the detection sensitivity of the sensor section 100 from varying depending on the color of the skin.

In the biological body information acquisition apparatus 200 according to the present embodiment, the main body section 160 and the sensor section 100 are separately incorporated in the belt 164, but the main body section 160 and the sensor section 100 may be integrated with each other and the integrated unit may be incorporated in the belt 164.

The biological body information acquisition apparatus 200 includes a control section 165, the sensor section 100, which is electrically connected to the control section 165, a storage section 167, an output section 168, and a communication section 169, as shown in FIG. 2. The biological body information acquisition apparatus 200 further includes a display section 162, which is electrically connected to the output section 168.

The sensor section 100 includes the imager 90 and the light guide plate 60. The imager 90 includes the light emitting section 40 and the light receiving section 10. Each of the light emitting section 40 and the light receiving section 10 is electrically connected to the control section 165. The light emitting section 40 has light emitting devices 43 (see FIG. 4), each of which emits near infrared light IL, the wavelength of which ranges from 700 to 2000 nm. The control section 165 drives the light emitting section 40 to cause it to output the near infrared light IL. The near infrared light IL propagates and is scattered in the human body M. Part of the near infrared light IL scattered in the human body M is received in the form of reflected light RL with light receiving devices 12 (see FIG. 4) in the light receiving section 10.

The control section 165 can cause the storage section 167 to store information on the reflected light RL received by the light receiving section 10. The control section 165 then causes the output section 168 to process the information on the reflected light RL. The output section 168 converts the information on the reflected light RL not only into image information on a blood vessel but also into information representing whether a specific component is contained in the blood and outputs the converted information. The control section 165 can further cause the display section 162 to display the converted image information on a blood vessel and information on a specific component in the blood. The control section 165 can then cause the communication section 169 to transmit the information to another information acquisition apparatus.

The control section 165 can further receive a program and other types of information from another information acquisition apparatus via the communication section 169 and cause the storage section 167 to store the program and other types of information. The communication section 169 may be a wire communication section, which is wired to another information acquisition apparatus, or a wireless communication section, such as a Bluetooth (registered trademark) communication section. The control section 165 may cause the display section 162 to display the program and other types of information stored in the storage section 167 in advance and current time and other types of information as well as the acquired information on a blood vessel and the blood. The storage section 167 may be a detachable memory.

Sensor Section

Figure 3:
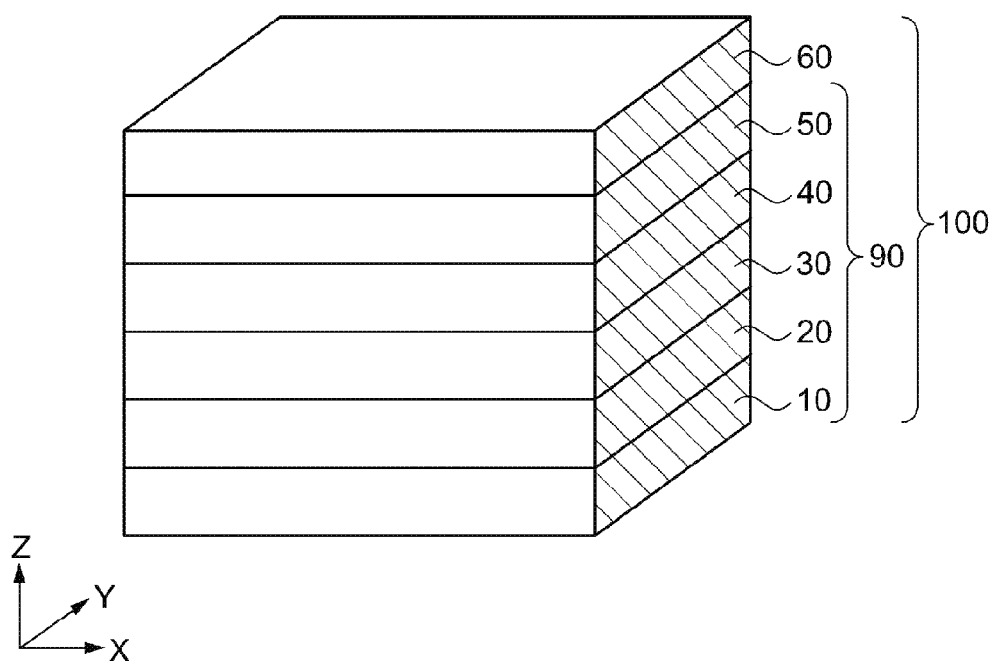
FIG. 3 is a schematic perspective view showing the configuration of a sensor section according to the first embodiment.
Figure 4:
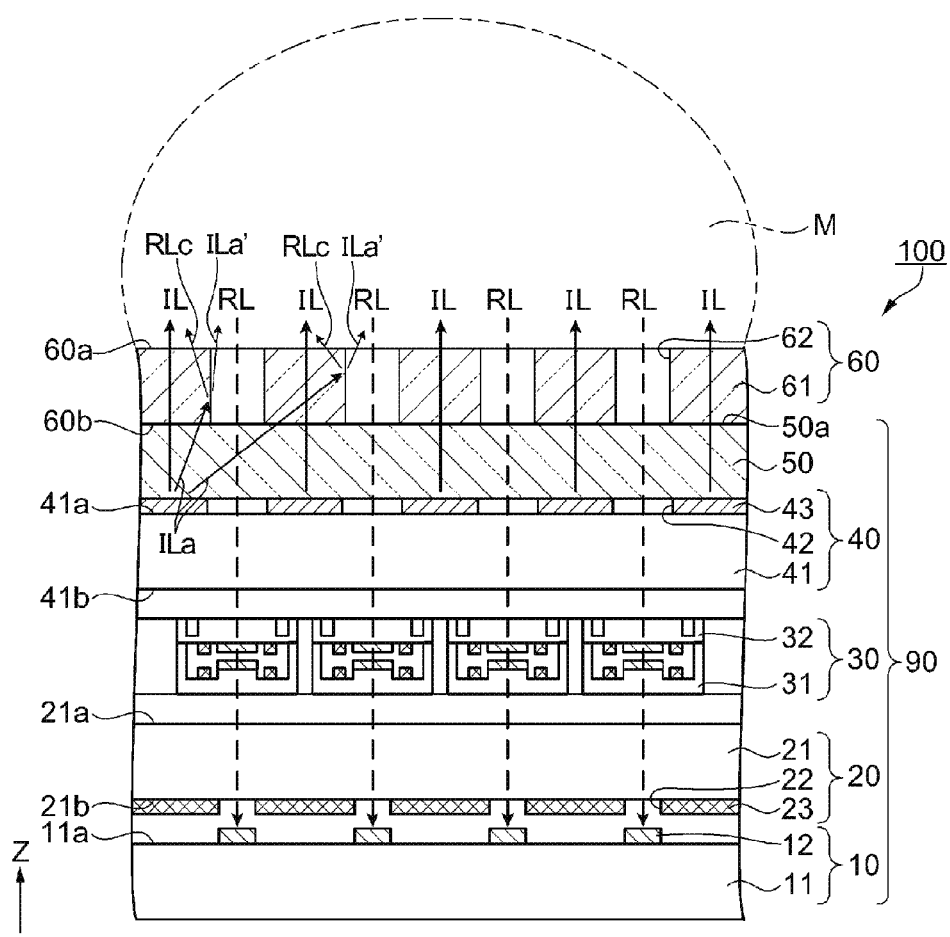
FIG. 4 is a schematic cross-sectional view showing the structure of the sensor section according to the first embodiment.
Figure 5A:
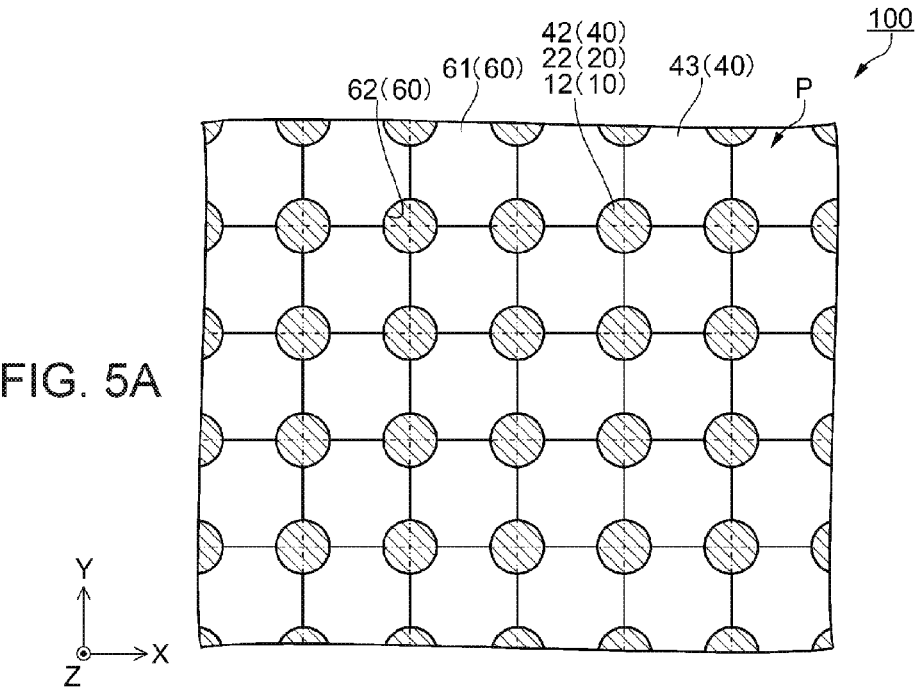
FIGS. 5A and 5B are schematic plan views showing the configuration of the sensor section according to the first embodiment.
Figure 5B:
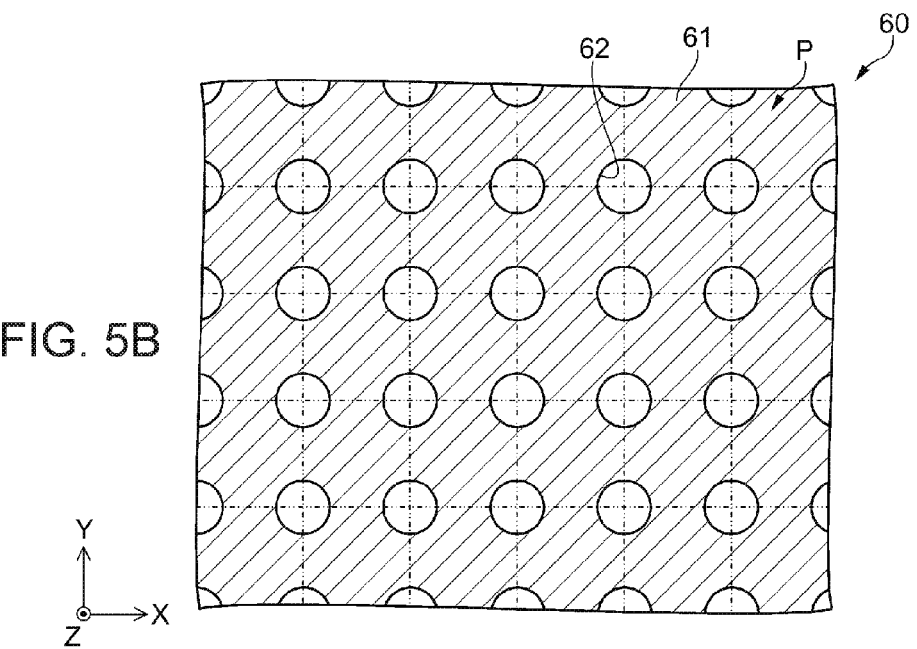

The sensor section 100 provided in the biological body information acquisition apparatus 200 according to the first embodiment will next be described with reference to FIGS. 3, 4, and 5A and 5B. FIG. 3 is a schematic perspective view showing the configuration of the sensor section according to the first embodiment. FIG. 4 is a schematic cross-sectional view showing the structure of the sensor section according to the first embodiment. FIGS. 5A and 5B are schematic plan views showing the configuration of the sensor section according to the first embodiment. Specifically, FIG. 5A shows the positional relationship of the planar arrangement of the light emitting devices and the light receiving devices with the light guide plate, and FIG. 5B shows a planar shape of the light guide plate.

The sensor section 100 according to the first embodiment includes the imager 90 and the light guide plate 60, as shown in FIG. 3. The imager 90 includes the light receiving section 10, a light blocking section 20, a spectrum controllable section 30, the light emitting section 40, and a protection section 50. Each of the light receiving section 10, the light blocking section 20, the spectrum controllable section 30, the light emitting section 40, the protection section 50, and the light guide plate 60 is a plate-shaped section, and on the light receiving section 10 are stacked the light blocking section 20, the spectrum controllable section 30, the light emitting section 40, the protection section 50, and the light guide plate 60 in this order.

The sensor section 100 has a case (not shown) that can accommodate the stacked body formed of the sections stacked on each other and can be attached to the belt 164 (see FIG. 1). The sensor section 100 is so attached to the belt 164 that the light guide plate 60 faces the human body M (see FIG. 2).

In the following description, let an X direction be the direction along one side of the stacked body described above, a Y direction be the direction along another side perpendicular to the one side, and a Z direction be the direction along the thickness direction of the stacked body described above. The Z direction is not only the direction in which the light guide plate 60 is layered but also the direction of a normal to the light receiving section 10 and the light emitting section 40. Further, viewing the sensor section 100 in the direction in which the light guide plate 60 is layered, that is, the direction of a normal to the light guide plate 60 (Z direction) is called a "plan view."

In FIG. 4, the +Z direction side is not only the upper side of the sensor section 100 but also the side where the sensor section 100 comes into contact with the human body M, and the −Z direction side is the lower side of the sensor section 100. The light emitting section 40 has a light-transmissive substrate main body 41, the light emitting devices 43, which are provided on an upper surface 41*a* of the substrate main body 41, and light transmissive portions 42 as shown in FIG. 4. Each of the light emitting devices 43 can, for example, be an LED device or an organic electroluminescence device. The light emitting devices 43 emit the near infrared light IL toward the human body M.

The protection section 50 is so provided as to be overlaid on the light emitting section 40. The protection section 50 is a transparent plate made, for example, of glass or any other inorganic material or acryl, polycarbonate, or any other resin material. The protection section 50 is intended to protect the light emitting devices 43 in the light emitting section 40 from moisture and oxygen. The protection section 50 is therefore preferably made of glass or any other inorganic material from a viewpoint of prevention of entry of moisture and oxygen.

The light guide plate 60 is so disposed as to be in contact with an upper surface 50*a* of the protection section 50. A lower surface 60*b* (surface facing protection section 50) of the light guide plate 60 is in contact with the surface 50*a* of the protection section 50, and the human body M is placed on an upper surface 60*a* of the light guide plate 60. The light guide plate 60 is formed of a transparent substrate 61 made of glass or any other inorganic material or acryl, polymethyl methacrylate, polycarbonate, or any other resin material.

The refractive index of the substrate 61 is preferably as close as possible to the refractive index of the protection section 50. The refractive index of glass is about 1.5. The refractive index of an acrylic resin ranges from about 1.49 to 1.53. The refractive index of polymethyl methacrylate ranges from about 1.49 to 1.6. The refractive index of polycarbonate is about 1.59.

The light guide plate 60 has a first portion and a second portion. Holes 62 are provided in the substrate 61 and pass through the substrate 61 in the Z direction, that is, in the direction of a normal to the light receiving section 10 and the light emitting section 40. The holes 62 form the first portion of the light guide plate 60, and the substrate 61 provided with the holes 62 (substrate portion excluding holes 62) forms the second portion of the light guide plate 60. The holes 62 are formed, for example, by etching or cutting performed on the substrate 61. In the light guide plate 60, the refractive index of the first portion is about 1.0 because the first portion (holes 62) is an air layer. The refractive index of the first portion of the light guide plate 60 is therefore smaller than the refractive index of the second portion of the light guide plate 60.

The near infrared light IL emitted from the light emitting devices 43 in the light emitting section 40 toward the human body M passes through the substrate 61, which forms the second portion of the light guide plate 60, and impinges on the human body M. The near infrared light IL having entered the human body M is scattered in the human body M. Part of the near infrared light IL scattered in the human body M passes in the form of the reflected light RL through the hole 62, which form the first portion of the light guide plate 60, passes through the light transmissive portions 42 in the light emitting section 40, and travels downward.

The spectrum controllable section 30 and the light blocking section 20 are disposed between the light emitting section 40 and the light receiving section 10. The spectrum controllable section 30 is disposed below the light emitting section 40. The spectrum controllable section 30 includes fixed substrates 31 and movable substrates 32. In the spectrum controllable section 30, a spectrum distribution (spectrum characteristic) of the reflected light RL passing through the spectrum controllable section 30 can be changed by electrical control of the gap between the fixed substrates 31 and the movable substrates 32. The near infrared light IL having passed through the spectrum controllable section 30 travels downward to the light blocking section 20.

The light blocking section 20 is disposed below the spectrum controllable section 30. The light blocking section 20 has a light transmissive substrate main body 21 and a light blocking film 23 provided on a lower surface 21*b* of the substrate main body 21. The light blocking film 23 has openings (pinholes) 22 formed therein in the positions corresponding to the arrangement of the light transmissive portions 42 in the light emitting section 40. Part of the reflected light RL having passed through the spectrum controllable section 30, that is, only reflected light RL having passed through the openings 22 is guided by the light receiving section 10 and received with the light receiving devices 12, and the remaining reflected light RL is blocked by the light blocking film 23.

The light receiving section 10 is an image sensor having high photosensitivity to near infrared light and has a substrate main body 11 and the plurality of light receiving devices 12 provided on the upper surface 11*a* of the substrate main body 11. The substrate main body 11 can be formed, for example, of a glass epoxy substrate or a ceramic substrate on which the light receiving devices 12 can be mounted. The substrate main body 11 is provided with an electrical circuit (not shown) including amplification transistors to which the light receiving devices 12 are connected and other components. Each of the light receiving devices 12 can, for example be a photodiode.

For example, when a photodiode is used as each of the light receiving devices 12, the reflected light RL incident on each of the light receiving devices 12 during a light exposure period causes junction leakage current in the light receiving device 12 to change in accordance with the amount of the incident reflected light RL, and the potential at the gate of the corresponding amplification transistor changes in accordance with the junction leakage current. In each of the light receiving devices 12, measuring a change in conductance of the amplification transistor resulting from the change in the gate potential during a readout period allows measurement of the amount of reflected light RL incident during the light exposure period. An image of a blood vessel in the human body M can be acquired on the basis of the amounts of light measured with the light receiving devices 12.

The sensor section 100 has unit pixels P, each of which serves as a unit for acquiring biological body information, as shown in FIG. 5A. The unit pixels P each have a roughly square shape and are arranged in a matrix along the X and Y directions. The light receiving devices 12 in the light receiving section 10 are arranged in a matrix along the X and Y directions so as to overlap with the corners of the unit pixels P in the plan view, as indicated by the oblique lines in FIG. 5A. Each of the light receiving devices 12 has a roughly circular light receiving surface in the plan view.

Further, the light emitting devices 43 in the light emitting section 40 are arranged in a matrix along the X and Y directions so as to coincide with the unit pixels P in the plan view. The light transmissive portions 42 in the light emitting section 40 are so arranged to coincide with the light receiving devices 12 in the plan view. Each of the light transmissive portions 42 has a roughly circular shape around the center of the corresponding light receiving device 12 in the plan view. Each of the openings 22 in the light blocking section 20 also has a roughly circular shape around the center of the corresponding light receiving device 12 in the plan view. The light transmissive portions 42 and the openings 22 may instead be so formed as to be greater than the outer shape of the light receiving devices 12.

In FIG. 5B, the substrate 61, which is the second portion of the light guide plate 60, is shown in the form of a hatched portion. The substrate 61 is provided with the holes 62, which form the first portion of the light guide plate 60 and overlap with the corners of the unit pixels P in the plan view. The holes 62 are so arranged as to coincide with the light receiving devices 12 in the plan view, as shown in FIG. 5A. The holes 62 may instead be so formed as to be greater than the outer shape of the light receiving devices 12. The substrate 61, which forms the second portion of the light guide plate 60, is so disposed as to coincide with the light emitting devices 43 in the plan view.

In the imager 90, the light blocking section 20, the spectrum controllable section 30, the light emitting section 40, and the protection section 50 are so arranged as to face each other with a gap therebetween and bonded to each other, for example, with an adhesive (not shown). The protection section 50 and the light guide plate 60 are bonded to each other, for example, with an adhesive. The protection section 50 and the light guide plate 60 are preferably in contact with each other.

In addition to the configuration described above, filters that remove light that belongs, for example, to a visible light wavelength range (400 to 700 nm) may be disposed in correspondence with the light transmissive portions 42 in the light emitting section 40 and the openings 22 in the light blocking section 20 to prevent visible light from contaminating the reflected light RL incident on the light receiving devices 12.

The configuration of the sensor section 100 is not limited to the configuration described above. For example, the light emitting section 40 may be configured to include the protection section 50 and may have a structure in which the protective section 50 seals the light emitting devices 43. Further, since the light having passed through the light transmissive portions 42 could be reflected off the interface between members having different refractive indices and therefore undesirably attenuated, the light emitting section 40 and the spectrum controllable section 30 may, for example, be so bonded to each other that a lower surface 41b of the substrate main body 41 in the light emitting section 40 is in contact with the spectrum controllable section 30. Further, the spectrum controllable section 30 and the light blocking section 20 may be so bonded to each other that the spectrum controllable section 30 is in contact with an upper surface 21a of the light blocking section 20. The bonded structure achieves more reliable positional relationship between the sections described above in the thickness direction thereof (Z direction).

Method for Acquiring Biological Body Information

Figure 6:
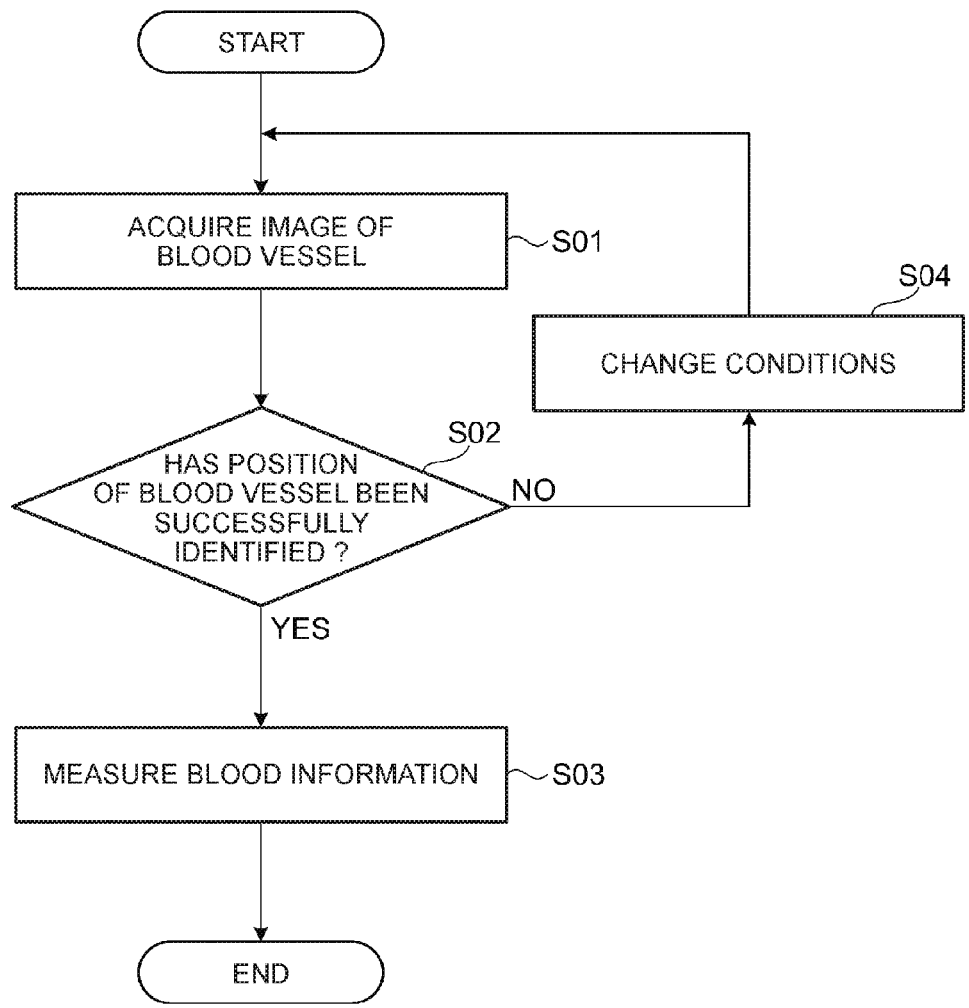
FIG. 6 is a flowchart showing how the biological body information acquisition apparatus acquires biological body information.

How the biological body information acquisition apparatus 200 according to the first embodiment acquires biological body information will next be described with reference to FIG. 6. FIG. 6 is a flowchart showing how the biological body information acquisition apparatus acquires biological body information. When the biological body information acquisition apparatus 200 is worn around a wrist of the human body M of a user of the biological body information acquisition apparatus 200, and the user operates the biological body information acquisition apparatus 200, the biological body information acquisition apparatus 200 starts measurement.

In step S01 shown in FIG. 6, the biological body information acquisition apparatus 200 causes all the light emitting devices 43 to emit the near infrared light IL toward the human body M. The reflected light RL reflected as part of the near infrared light IL scattered in the human body M toward the biological body information acquisition apparatus 200 is then received with all the light receiving devices 12. The biological body information acquisition apparatus 200 acquires an image of a blood vessel in the human body M on the basis of a detection signal according to the amount of light received with each of the light receiving devices 12.

In the following step S02, the biological body information acquisition apparatus 200 detects the pattern of the blood vessel in the human body M from the image of the blood vessel acquired in step S01 and evaluates whether or not the position of the blood vessel has been successfully identified. When a result of the evaluation in step S02 shows that the position of the blood vessel has been successfully identified (step S02: YES), the biological body information acquisition apparatus 200 proceeds to the process in step S03.

In the subsequent step S03, the biological body information acquisition apparatus 200 causes the light emitting device 43 corresponding to the position of the blood vessel identified in step S02 to emit the near infrared light IL toward the blood vessel in the human body M. The reflected light RL reflected from the human body M toward the biological body information acquisition apparatus 200 is then received with the light receiving device 12 corresponding to the position of the blood vessel identified in step S02. The biological body information acquisition apparatus 200 measures a specific component in the blood in the human body M and other types of blood information on the basis of a detection signal according to the amount of light received with the light receiving device 12 and completes the measurement procedure.

On the other hand, when a result of the evaluation in step S02 shows that the position of the blood vessel has not successfully identified (step S02: NO), the biological body information acquisition apparatus 200 proceeds to the process in step S04. In step S04, the biological body information acquisition apparatus 200 changes a condition under which an image of a blood vessel is acquired in step S01. Examples of the condition under which an image of a blood vessel is acquired may include the intensity of the near infrared light IL emitted from the light emitting devices 43 and the light exposure period for which the light receiving devices 12 receive the reflected light RL.

After a measurement condition is changed in step S04, the biological body information acquisition apparatus 200 returns to the process in step S01 and repeats the processes in steps S01 to S03.

Even when a measurement condition is changed in step S04, the position of the blood vessel cannot be identified in step S02 in some cases. Further, even when the position of the blood vessel is successfully identified in step S02, the measurement of blood information cannot be performed in a stable manner in step S03 in some cases. The inventors of the present application have studied causes that result in the undesirable cases described above and found that as one cause, the light received with the light receiving devices 12 contains a large amount of light other than the reflected light RL (signal light) scattered and reflected in the human body M, more specifically, light reflected off the surface (skin) of the human body M (noise light).

Figure 12:
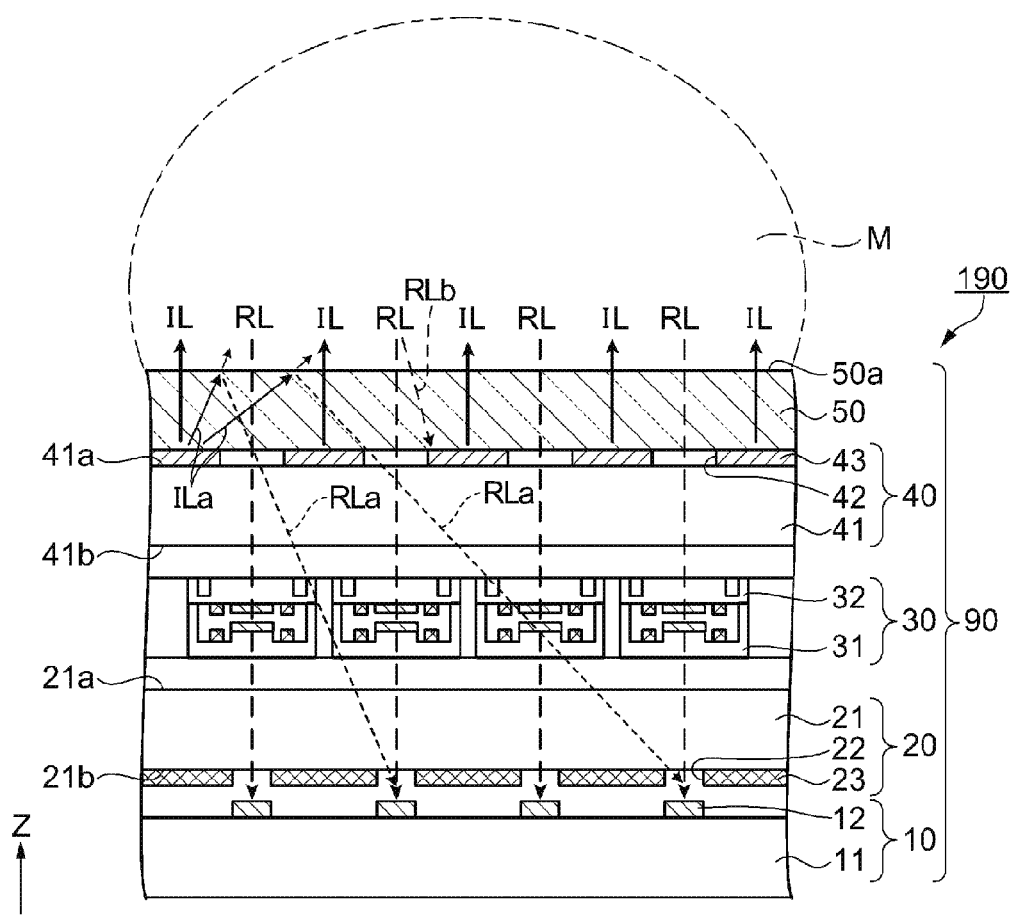
FIG. 12 is a schematic cross-sectional view showing the structure of a sensor section as Comparative Example.

An effect of the light reflected off the surface of the human body M will be described below with reference to FIG. 12. FIG. 12 is a schematic cross-sectional view showing the structure of a sensor section as Comparative Example. A sensor section 190 as Comparative Example shown in FIG. 12 has the same configuration as that of the sensor section 100 according to the present embodiment except that the sensor section 190 includes the imager 90 but no light guide plate 60.

The sensor section 190, which includes no light guide plate 60, is so disposed that the imager 90 (surface 50a of protection section 50) is in contact with the human body M, as shown in FIG. 12. The near infrared light IL emitted from the light emitting devices 43 in the light emitting section 40 ideally travels along the direction of a normal to the light emitting section 40 (Z direction), but near infrared light ILa, which is emitted in all directions from each of the light emitting devices 43 and travels obliquely with respect to the direction of a normal to the light emitting section 40 (hereinafter also referred to as oblique light ILa), is also present. The oblique light ILa is so emitted as to diffuse outward from the center position of each of the light emitting devices 43 when viewed in a plane.

When radiated toward the human body M, the oblique light ILa is partially reflected off the interface between the protection section 50 (surface 50a) and the human body M (skin) toward the side opposite the human body M. The part of the oblique light ILa or oblique light ILa reflected off the interface between the protection section 50 and the human body M forms reflected light RLa, which is noise light, unlike the reflected light RL (signal light) having been scattered and reflected in the human body M. When the reflected light RLa (noise light) is received with any of the light receiving devices 12, the signal-to-noise ratio (S/N ratio) in the acquisition of an image of a blood vessel undesirably decreases. The noise light is one cause of the case where the position of the blood vessel cannot be identified in S02 and the case where the measurement of blood information cannot be performed in a stable manner in step S03.

On the other hand, the reflected light RL scattered and reflected in the human body M contains reflected light RLb, which travels obliquely with respect to the direction of a normal to the light emitting section 40. A large part of the obliquely traveling reflected light RLb (signal light) is undesirably blocked by the light emitting devices 43 in the light emitting section 40 and the light blocking film 23 in the light blocking section 20 and is not received with any of the light receiving devices 12.

Therefore, to reliably identify the position of the blood vessel in step S02 and measure blood information in a stable manner in step S03, it is desirable to minimize the amount of noise light (reflected light RLa, for example) received with the light receiving devices 12 and maximize the signal light (reflected light RLb, for example) received with the light receiving devices 12.

To acquire an image of a blood vessel, it is desirable to achieve a state in which the entire surface 50a of the protection section 50 comes into uniform contact with a wrist of the human body M. However, due to the fact that the surface 50a of the protection section 50 is roughly flat but the surface of a wrist of the human body M is not flat, air and moisture (sweat, for example) present between the human body M and the protection section 50 undesirably produce a portion where the human body M does not come into direct contact with the protection section 50 in some cases.

When air is interposed between the human body M and the protection section 50, the fact that the difference in refractive index between the protection section 50 and the air is greater than the difference between the human body M and the protection section 50 in direct contact with each other tends to cause reflection at the interface between the protection section 50 and the air, resulting in an increase in the amount of reflected light RLa (noise light). When moisture is present between the human body M and the protection section 50, optical conditions between the human body M and the protection section 50 become unstable due, for example, to an effect of the absorption spectrum of the moisture.

The sensor section 100 according to the first embodiment includes the light guide plate 60 layered on the imager 90 (protection section 50), and the surface 60a of the light guide plate 60 is so disposed as to come into contact with the human body M, as shown in FIG. 4. As described above, the light guide plate 60 has the first portion (holes 62) so disposed as to coincide with the light receiving devices 12 in the plan view and the second portion (substrate 61) so disposed as to coincide with the light emitting devices 43 in the plan view.

The oblique light ILa emitted from each of the light emitting devices 43 passes through the second portion (substrate 61) of the light guide plate 60 and reaches the interface with the first portion (holes 62). Since the first portion (holes 62) is an air layer and the refractive index of the first portion is therefore smaller than the refractive index of the second portion (substrate 61), the oblique light ILa is partially reflected off the interface between the first portion and the second portion, and reflected light RLc, which has been partially reflected off the interface, travels toward the human body M. The reflected light RLc, which has been partially reflected off the interface, travels when viewed in a plane toward the position corresponding to the center of the light emitting device 43 from which the reflected light RLc originates. Therefore, even when the reflected light RLc is further partially reflected off the interface between the second portion (substrate 61) of the light guide plate 60 and the human body M, most of the partially reflected light is blocked by the light emitting device 43.

Further, part of the oblique light ILa emitted from each of the light emitting devices 43 or incident light ILa', which is incident from the second portion (substrate 61) of the light guide plate 60 on the first portion (holes 62), is refracted at a greater angle than the angle of incidence. The angle of incidence of the incident light ILa' incident from the first portion (holes 62) of the light guide plate 60 on the human body M is therefore smaller than the angle of incidence of the oblique light ILa in an imaginary case in which it travels straightforward and impinges on the human body M. Reflection at the interface with the human body M (skin) is therefore unlikely to occur.

As described above, the sensor section 100 according to the first embodiment, which includes the light guide plate 60 disposed between the imager 90 and the human body M, allows reduction in the amount of reflected light RLa (see FIG. 12), which is produced when the oblique light ILa emitted from each of the light emitting devices 43 is reflected off the interface between the light guide plate 60 and the human body M (skin) to form noise light. As a result, the signal-to-noise ratio (S/N ratio) of the light received with the light receiving devices 12 can be improved as compared with the S/N ratio provided by the sensor section 190 shown in FIG. 12, whereby the identification of the position of a blood vessel and the measurement of blood information can be more reliably performed.

In the sensor section 100 according to the first embodiment, in which the light guide plate 60 has the first portion (holes 62), air and moisture between the second portion (substrate 61) of the light guide plate 60 and the human body Mare likely to enter the first portion (holes 62). As a result, the second portion (substrate 61) of the light guide plate 60 adheres with the human body M in an improved manner, and the amount of reflected light RLa (noise light) reflected off the surface (skin) of the human body M is therefore smaller than the amount of reflected light RLa produced in the sensor section 190 shown in FIG. 12, whereby the optical conditions between the human body M and the imager 90 (protection section 50) are stabilized.

Second Embodiment

A second embodiment is substantially the same as the first embodiment in terms of the configuration of the biological body information acquisition apparatus and the method for acquiring biological body information but differs therefrom in terms of the configuration of the light guide plate in the sensor section. The following description will be made of the configuration and an effect of the light guide plate according to the second embodiment in terms of differences from those in the first embodiment.

Sensor Section

Figure 7:
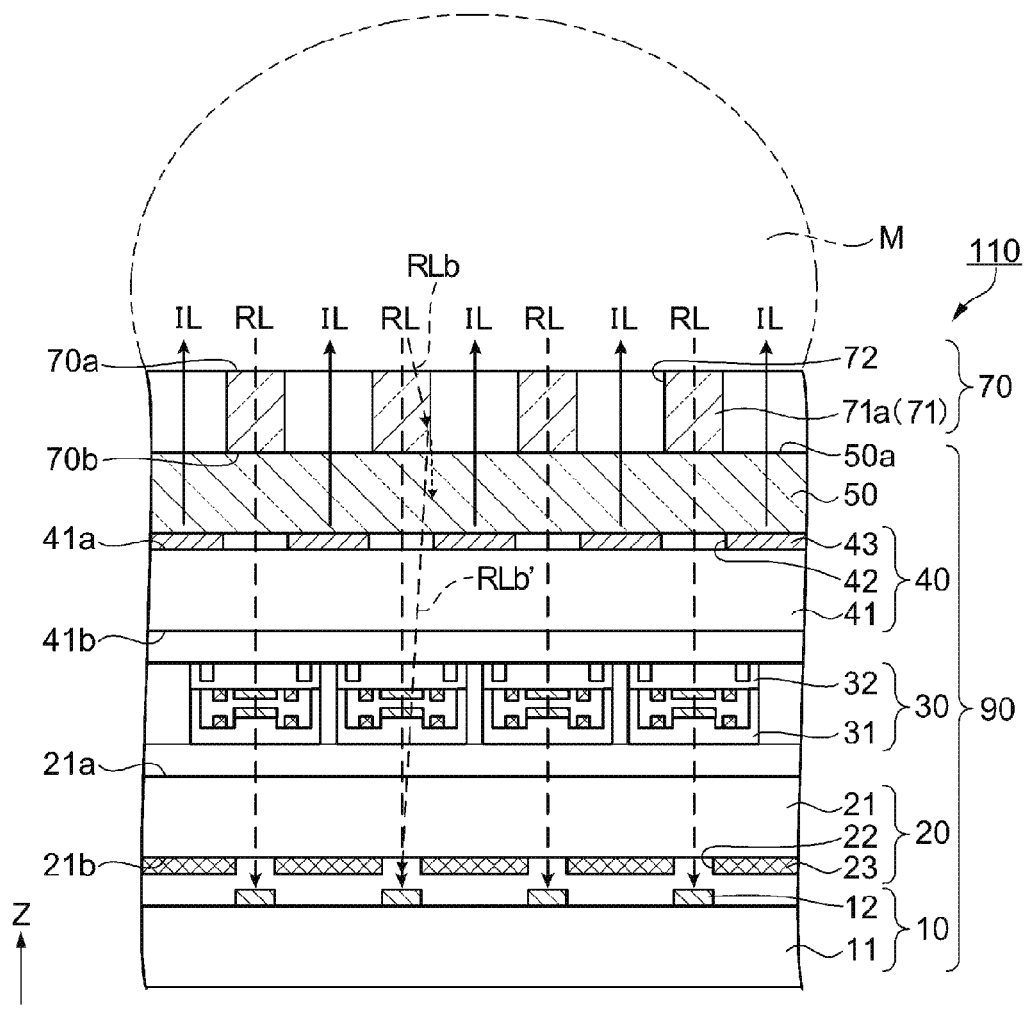
FIG. 7 is a schematic cross-sectional view showing the structure of a sensor section according to a second embodiment.
Figure 8A:
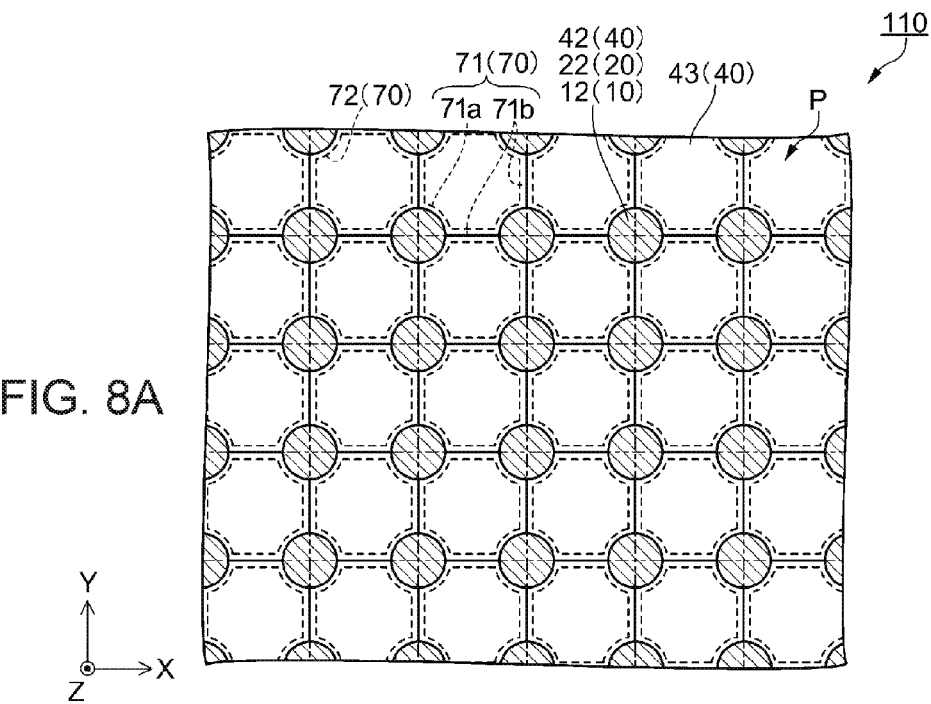
FIGS. 8A and 8B are schematic plan views showing the configuration of the sensor section according to the second embodiment.
Figure 8B:
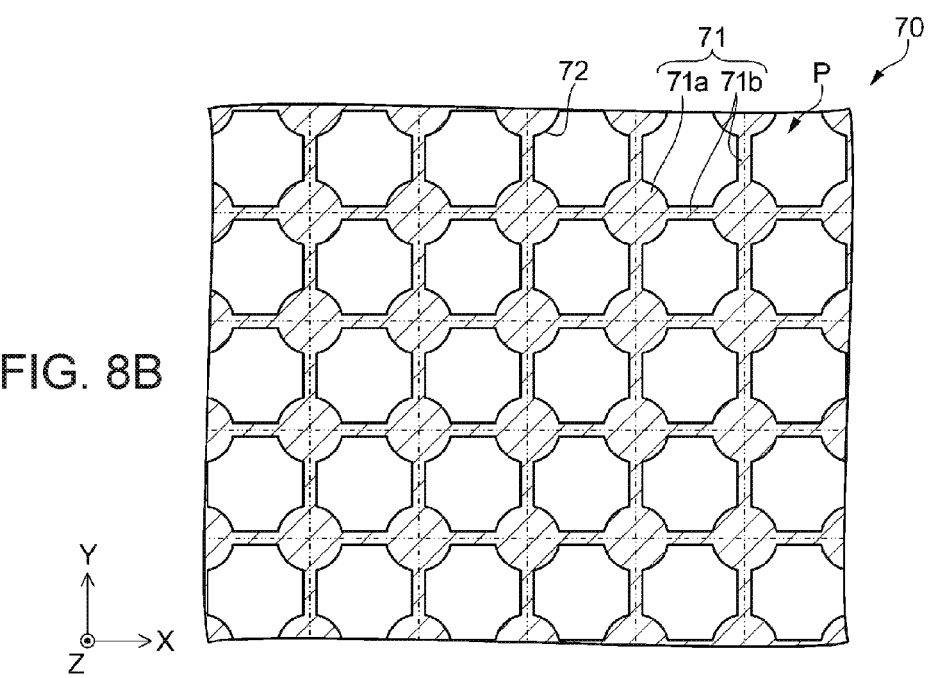

A sensor section 110 according to the second embodiment will be described with reference to FIG. 7 and FIGS. 8A and 8B. FIG. 7 is a schematic cross-sectional view showing the structure of the sensor section according to the second embodiment. FIGS. 8A and 8B are schematic plan views showing the configuration of the sensor section according to the second embodiment. Specifically, FIG. 8A shows the positional relationship of the planar arrangement of the light emitting devices and the light receiving devices with the light guide plate, and FIG. 8B shows a planar shape of the light guide plate.

The sensor section 110 according to the second embodiment includes the imager 90 and a light guide plate 70, as shown in FIG. 7. The light guide plate 70 is layered on the imager 90 and so disposed as to be in contact with the upper surface 50a of the protection section 50. The light guide plate 70 according to the second embodiment is formed of a transparent substrate 71 made of the same material as that of the light guide plate 60 (substrate 61) according to the first embodiment.

The light guide plate 70 has a first portion and a second portion. Holes 72 are provided in the substrate 71 and pass through the substrate 71 in the Z direction (direction of a normal to the light receiving section 10 and the light emitting section 40). The holes 72 form the second portion of the light guide plate 70, and the substrate 71 provided with the holes 72 (substrate portion excluding holes 72) forms the first portion of the light guide plate 70. In the light guide plate 70, the refractive index of the first portion (portion of substrate 71 excluding holes 72) is greater than the refractive index of the second portion (holes 72) because the second portion (holes 72) is an air layer.

In FIG. 8B, the substrate 71, which is the first portion of the light guide plate 70, is shown in the form of a hatched portion. The substrate 71 has portions 71a, which overlap with the corners of the unit pixels P in the plan view, and portions 71b, part of which extends in the X direction along the one side of each of the unit pixels P and the remainder of which extends in the Y direction along another side of each of the unit pixels P, as shown in FIG. 8B. The portions 71b are portions that connect the portions 71a located at the corners of the unit pixels P to each other in the X and Y directions and support the portions 71a.

The portions 71a of the substrate 71, which forms the first portion of the light guide plate 70, have a roughly circular shape around the centers of the light receiving devices 12 in the plan view and are so arranged as to coincide with the light receiving devices 12, as shown in FIG. 8A. The portions 71a may instead be so formed as to be greater than the outer shape of the light receiving devices 12. The holes 72, which form the second portion of the light guide plate 70, are so arranged as to coincide with the light emitting devices 43 in the plan view. Therefore, in the light guide plate 70 according to the second embodiment, the positional relationship between the first portion (substrate 71) and the second portion (holes 72) with respect to the light receiving devices 12 and the light emitting devices 43 is reversed from the positional relationship in the light guide plate 60 according to the first embodiment.

The near infrared light IL emitted from the light emitting devices 43 in the light emitting section 40 toward the human body M passes through the holes 72, which form the second portion of the light guide plate 70, and impinges on the human body M, as shown in FIG. 7. The reflected light RL, which is the near infrared light IL scattered and reflected in the human body M, passes through the substrate 71 (portions 71a), which forms the first portion of the light guide plate 70, passes through the light transmissive portions 42 in the light emitting section 40 and travels downward, passes through the spectrum controllable section 30 and the light blocking section 20 (openings 22), and is received with the light receiving devices 12 in the light receiving section 10.

The reflected light RLb scattered in the human body M and traveling obliquely with respect to the direction of a normal to the light emitting section 40 passes through the substrate 71 (portions 71a), which forms the first portion of the light guide plate 70, and reaches the interface with the second portion (holes 72). Since the second portion (holes 72) is an air layer and the refractive index of the first portion (substrate 71) is therefore greater than the refractive index of the second portion, the reflected light RLb is partially reflected off the interface between the first portion and the second portion. Reflected light RLb', which has been partially reflected off the interface, passes through the light transmissive portions 42 in the light emitting section 40 and travels downward, passes through the spectrum controllable section 30 and the light blocking section 20 (openings 22), and is guided to the light receiving devices 12 in the light receiving section 10.

The reflected light RLb', which is part of the reflected light RLb (signal light) and has not been received with the light receiving devices 12 in the sensor section 190 shown in FIG. 12, is allowed to be received with the light receiving devices 12 in the sensor section 110 according to the second embodiment. That is, in the sensor section 110 according to the second embodiment, the amount of signal light received with the light receiving devices 12 can be greater than the amount of signal light received in the light receiving section 190. As a result, the signal-to-noise ratio (S/N ratio) in the acquisition of an image of a blood vessel can be improved, whereby the identification of the position of a blood vessel and the measurement of blood information can be more reliably performed.

In the sensor section 110 according to the second embodiment, in which the light guide plate 70 has the second portion (holes 72), air and moisture between the first portion (substrate 71) of the light guide plate 70 and the human body Mare likely to enter the second portion (holes 72). As a result, the first portion (substrate 71) of the light guide plate 70 adheres with the human body M in an improved manner, whereby the optical conditions between the human body M and the imager 90 (protection section 50) can be stabilized as compared with those in the sensor section 190.

Third Embodiment

Figure 9:
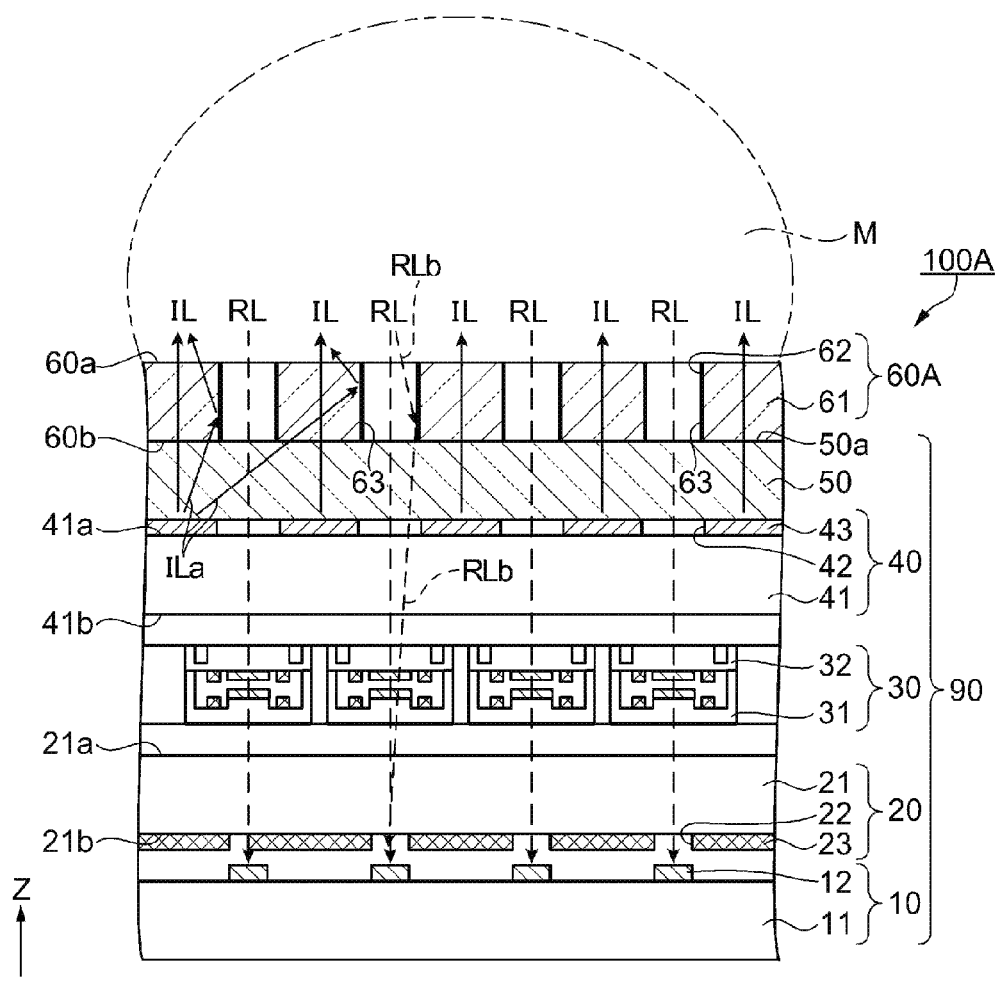
FIG. 9 is a schematic cross-sectional view showing the structure of a sensor section according to a third embodiment.

A third embodiment is substantially the same as the first embodiment in terms of the configuration of the biological body information acquisition apparatus and the method for acquiring biological body information but differs therefrom in terms of the configuration of the light guide plate in the sensor section. The following description will be made of the configuration and an effect of the light guide plate according to the third embodiment in terms of differences from those in the first embodiment.
Sensor Section A sensor section 100A according to the third embodiment will be described with reference to FIG. 9. FIG. 9 is a schematic cross-sectional view showing the structure of the sensor section according to the third embodiment.

The sensor section 100A according to the third embodiment includes the imager 90 and a light guide plate 60A, as shown in FIG. 9. The light guide plate 60A according to the third embodiment differs from the light guide plate 60 according to the first embodiment in that a reflection film 63 is formed on each wall surface (surface along Z direction) of the substrate 61, in which the holes 62 are formed. The reflection film 63 is formed, for example, of a metal film made, for example, of chromium (Cr), aluminum (Al), or gold (Au).

In the light guide plate 60A according to the third embodiment, the reflection films 63, which are formed on the wall surfaces of the substrate 61, in which the holes 62 are formed, are present at the interface between the second portion (substrate 61) and the first portion (holes 62). The oblique light ILa emitted from the light emitting devices 43, when it reaches the interface between the second portion (substrate 61) and the first portion (holes 62), is therefore totally reflected off the reflection films 63 and directed toward the human body M. The amount of noise light (reflected light RLa shown in FIG. 12) can therefore be smaller than the amount of noise light received through the light guide plate 60 according to the first embodiment.

On the other hand, the reflected light RLb (signal light) traveling obliquely with respect to the direction of a normal to the light emitting section 40, when it reaches the interface between the first portion (holes 62) and the second portion (substrate 61), is totally reflected off the reflection films 63 and guided to the light receiving devices 12 in the light receiving section 10. The amount of signal light received with the light receiving devices can therefore be greater than the amount of signal light received through the light guide plate 60 according to the first embodiment.

As described above, the sensor section 100A according to the third embodiment allows the amount of noise light (reflected light RLa) received with the light receiving devices 12 to be further reduced and the amount of signal light (reflected light RLb) received with the light receiving devices 12 to be further increased as compared with those in the sensor section 100 according to the first embodiment. As a result, the signal-to-noise ratio (S/N ratio) in the acquisition of an image of a blood vessel can be further improved, whereby the identification of the position of a blood vessel and the measurement of blood information can be still more reliably performed.

Fourth Embodiment

Figure 10:
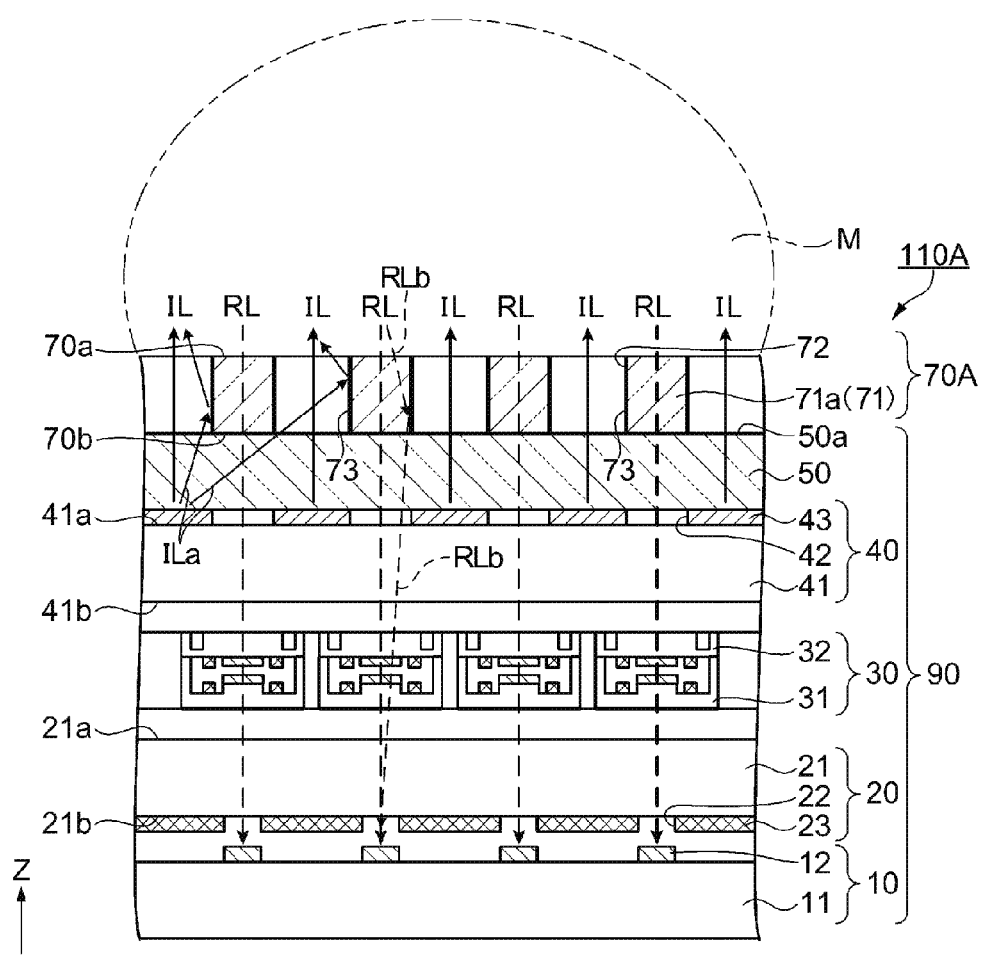
FIG. 10 is a schematic cross-sectional view showing the structure of a sensor section according to a fourth embodiment.

A fourth embodiment is substantially the same as the second embodiment in terms of the configuration of the biological body information acquisition apparatus and the method for acquiring biological body information but differs therefrom in terms of the configuration of the light guide plate in the sensor section. The following description will be made of the configuration and an effect of the light guide plate according to the fourth embodiment in terms of differences from those in the second embodiment.
Sensor Section A sensor section 110A according to the fourth embodiment will be described with reference to FIG. 10. FIG. 10 is a schematic cross-sectional view showing the structure of the sensor section according to the fourth embodiment.

The sensor section 110A according to the fourth embodiment includes the imager 90 and a light guide plate 70A, as shown in FIG. 10. The light guide plate 70A according to the fourth embodiment differs from the light guide plate 70 according to the second embodiment in that a reflection film 73 is formed on each wall surface (surface along Z direction) of the substrate 71, in which the holes 72 are formed. The reflection film 73 is formed of the same metal film of which each of the reflection films 63 is formed.

In the light guide plate 70A according to the fourth embodiment, the reflection films 73, which are formed on the wall surfaces of the substrate 71, in which the holes 72 are formed, are present at the interface between the first portion (substrate 71) and the second portion (holes 72). The oblique light ILa emitted from the light emitting devices 43, when it reaches the interface between the second portion (holes 72) and the first portion (substrate 71), is therefore totally reflected off the reflection films 73 and directed toward the human body M. The amount of noise light (reflected light RLa shown in FIG. 12) can therefore be smaller than the amount of noise light received through the light guide plate 70 according to the second embodiment.

On the other hand, the reflected light RLb (signal light) traveling obliquely with respect to the direction of a normal to the light emitting section 40, when it reaches the interface between the first portion (substrate 71) and the second portion (holes 72), is totally reflected off the reflection films 73 and received with the light receiving devices 12 in the light receiving section 10. The amount of signal light received with the light receiving devices can therefore be greater than the amount of signal light received through the light guide plate 70 according to the second embodiment.

As described above, the sensor section 110A according to the fourth embodiment allows the amount of noise light (reflected light RLa) received with the light receiving devices 12 to be further reduced and the amount of signal light (reflected light RLb) received with the light receiving devices 12 to be further increased as compared with those in the sensor section 110 according to the second embodiment. As a result, the signal-to-noise ratio (S/N ratio) in the acquisition of an image of a blood vessel can be further improved, as in the sensor section 100A according to the third embodiment, whereby the identification of the position of a blood vessel and the measurement of blood information can be still more reliably performed.

Each of the embodiments described above only shows an aspect of the invention and can be arbitrarily changed and applied within the scope of the invention. The following variations are, for example, conceivable.

Variation 1

In the embodiments described above, the sensor sections 100, 100A, 110, and 110A have the configurations in which the light guide plates 60, 60A, 70, and 70A are layered on the protection section 50 in the imager 90, but the invention is not limited to such a form. The protection section 50 may be integrated with each of the light guide plates 60, 60A, 70, and 70A.

Figure 11:
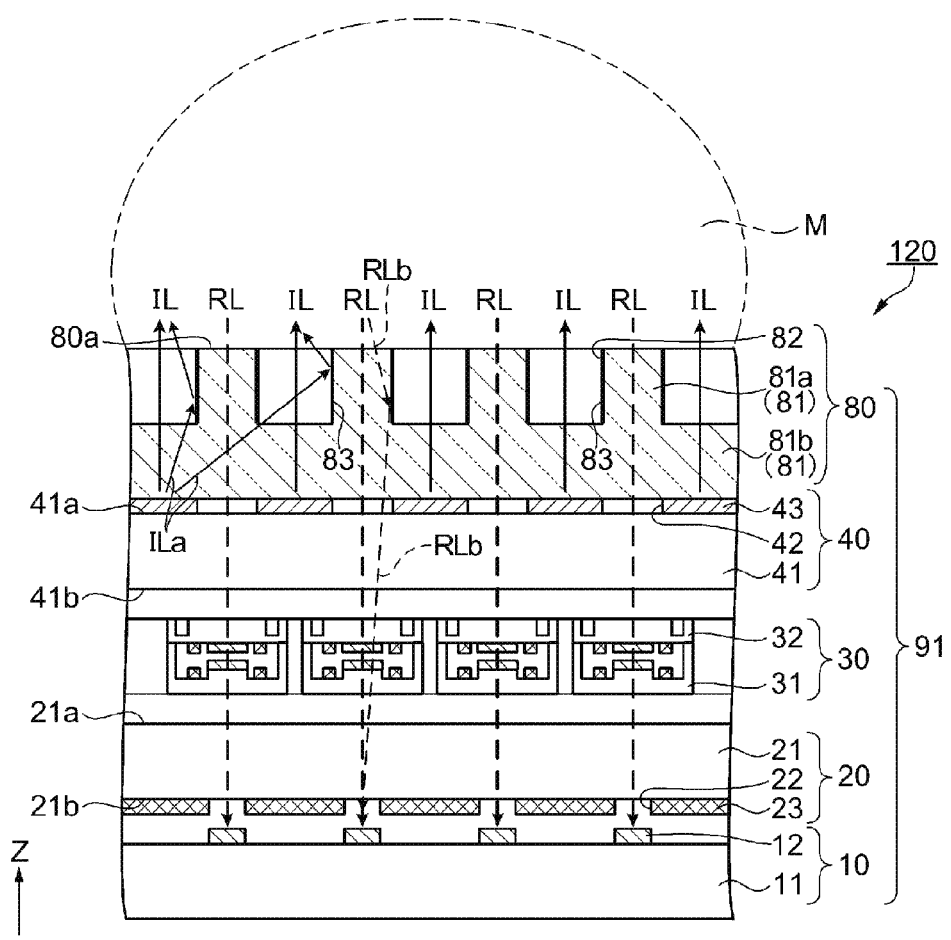
FIG. 11 is a schematic cross-sectional view showing the structure of a sensor section according to Variation 1.

FIG. 11 is a schematic cross-sectional view showing the structure of a sensor section according to Variation 1. FIG. 11 shows a case where a sensor section 120 according to Variation 1 includes a section formed of the protection section 50 and the light guide plate 70A according to the fourth embodiment integrated with each other. An imager 91 provided in the sensor section 120 has a light guide plate 80 integrated with a protection section. The light guide plate 80 is formed of a substrate 81 made of the same material as those of the substrates 61 and 71 in the embodiments described above. The substrate 81 is provided with holes 82, which are formed through an upper surface 80a but do not completely pass through the substrate 81. The substrate 81 has an upper portion 81a and a lower portion 81b. The upper portion 81a corresponds, for example, to the substrate 71 (portions 71a) of the light guide plate 70 shown in FIG. 8B. The lower portion 81b is a flat-plate-shaped portion corresponding to the protection section 50 in FIG. 7. In the light guide plate 80, since the upper portion 81a can be supported by the lower portion 81b, no portion corresponding to the portions 71b of the light guide plate 70 shown in FIG. 8B is required. A reflection film 83 formed of a metal film is formed on each wall surface (surface along Z direction) of the upper portion 81a, in which the holes 82 are formed.

The thus configured light guide plate 80 provides the same advantageous effects as those provided by the fourth embodiment. Since the lower portion 81b, which corresponds to the protection section 50, and the upper portion 81a, are formed integrally with each other in the same substrate 81, the reflection at the interface between the protection section 50 and the light guide plate 70A, which occurs in the fourth embodiment, can be eliminated, whereby the amount of noise light can be further reduced. The upper portions 81a of the substrate 81 may instead be a portion corresponding to the substrate 61 of the light guide plate 60 shown in FIG. 5B.

Variation 2

In the third embodiment, the fourth embodiment, and Variation 1, the reflection films 63, 73, and 83, each of which is formed of a metal film, are formed on the wall surfaces of the substrate 61, the substrate 71, and the upper portion 81a of the substrate 81, but the invention is not limited to such a form. Each of the reflection films 63, 73 and 83 may be replaced with a light blocking film made, for example, of a light-blocking resin material. In this configuration, since the oblique light ILa is blocked by the light blocking films, whereby the amount of noise light received with the light receiving devices 12 can be reduced.

Variation 3

In the embodiments described above, description of the information acquisition apparatus has been made with reference to the biological body information acquisition apparatus 200, which is a portable information terminal capable of acquiring information, such as image information on a blood vessel and information on a specific component in the blood, but the invention is not limited to such a form. The information acquisition apparatus may instead be an information acquisition apparatus having any other different form, such as an immobile information acquisition apparatus, or a biological body authentication apparatus that acquires image information on a vein in a finger and compares the image information with preregistered image information on veins to identify an individual. The information acquisition apparatus may still instead be a solid-state imaging apparatus that captures an image of a fingerprint, the iris of an eyeball, and other body parts.

The entire disclosure of Japanese Patent Application No. 2015-013022 filed on Jan. 27, 2015 is hereby incorporated herein by reference.

What is claimed is:

1. An information acquisition apparatus comprising:
an imager including
a light emitting device that emits light toward an object, and
a light receiving device that receives light from the object; and
a light guide plate that is so provided as to be layered on the imager on the side thereof facing the object,
wherein the light guide plate has light transmissivity in a direction in which the light guide plate is layered on the imager and has a first portion and a second portion having refractive indices different from each other, the first portion is so disposed as to coincide with the light receiving device when viewed in the direction, and the second portion is so disposed as to coincide with the light emitting device when viewed in the direction, and
the light receiving device, light emitting device, and light guide plate are stacked in the order of the light receiving device, light emitting device, and light guide plate, where the light guide plate is layered on the side of the imager facing the object.

2. The information acquisition apparatus according to claim 1,
wherein the refractive index of the first portion is smaller than the refractive index of the second portion.

3. The information acquisition apparatus according to claim 2,
wherein the light guide plate is provided with a hole along the direction, in which the light receiving device and the light emitting device are arranged, and
the hole forms the first portion and a remaining portion of the light guide plate other than the hole forms the second portion.

4. The information acquisition apparatus according to claim 1,
   wherein the refractive index of the first portion is greater than the refractive index of the second portion.

5. The information acquisition display apparatus according to claim 4,
   wherein the light guide plate is provided with a hole along the direction, in which the light receiving device and the light emitting device are arranged, and
   the hole forms the second portion and a remaining portion of the light guide plate other than the hole forms the first portion.

6. The information acquisition apparatus according to claim 1,
   wherein a reflection film is formed at an interface between the first portion and the second portion.

7. The information acquisition apparatus according to claim 6,
   wherein the reflection film is a metal film.

\* \* \* \* \*